United States Patent
Lokhoff et al.

(10) Patent No.: US 6,909,920 B2
(45) Date of Patent: Jun. 21, 2005

(54) SYSTEM AND METHOD FOR POSITIONING AN IMPLANTABLE MEDICAL DEVICE WITHIN A BODY

(75) Inventors: Nicolaas M. Lokhoff, He Kerkrade (NL); David L. Thompson, Andover, MN (US)

(73) Assignee: Medtronic, Inc., Minneapolis, MN (US)

(*) Notice: Subject to any disclaimer, the term of this patent is extended or adjusted under 35 U.S.C. 154(b) by 392 days.

(21) Appl. No.: 09/844,628

(22) Filed: Apr. 27, 2001

(65) Prior Publication Data

US 2002/0161423 A1 Oct. 31, 2002

(51) Int. Cl.$^7$ ................................... A61N 1/05
(52) U.S. Cl. ..................... 607/127; 607/119; 607/131
(58) Field of Search ..................... 607/119, 126–128, 607/131, 122; 600/375

(56) References Cited

U.S. PATENT DOCUMENTS

| | | | |
|---|---|---|---|
| 4,106,512 A | 8/1978 | Bisping | 128/418 |
| 4,311,153 A | 1/1982 | Smits | 128/785 |
| 4,402,330 A | 9/1983 | Lindemans | 128/786 |
| 4,570,642 A | 2/1986 | Kane et al. | 128/785 |
| 4,886,074 A | 12/1989 | Bisping | 128/785 |
| 4,913,147 A | 4/1990 | Fahlstrom et al. | 128/419 P |
| 5,129,394 A | 7/1992 | Mehra | 128/419 PG |
| 5,259,394 A | * 11/1993 | Bens | 607/127 |
| 5,378,239 A | * 1/1995 | Termin et al. | 604/104 |
| 5,423,772 A | 6/1995 | Lurie et al. | 604/282 |
| 5,456,708 A | * 10/1995 | Doan et al. | 607/127 |

(Continued)

FOREIGN PATENT DOCUMENTS

| FR | 2322582 | 9/1976 | A61H/31/00 |
|---|---|---|---|
| FR | 2558376 | 1/1984 | A61N/1/05 |

OTHER PUBLICATIONS

Brecker et al., "Effects of Dual Chamber Pacing With Short Atrioventricular Delay in Dilated Cardiomyopathy," *Lancet*, vol. 340, p. 1308–12 (Nov. 1992).

Cazeau et al., "Four Chamber Pacing in Dilated Cardiomyopathy," *PACE*, p. 1974–79 (Nov. 1994).

Fontaine, G. et al., "Electrophysiology of Pseudofunction," *Cardiac Pacing, State of the Art*, C.I. Meere (ed.), Pacesymp., Montreal (1979).

Xiao HB et al., "Effect of Left Bundle Branch Block on Diastolic Function in Dilated Cardiomyopathy," *Br. Heart J*, p. 443–47 (1991).

*Primary Examiner*—Angela D. Sykes
*Assistant Examiner*—Roderick Bradford
(74) *Attorney, Agent, or Firm*—Daniel G. Chapik; Girma Wolde-Michael (57) ABSTRACT

A transvenous implantable medical device adapted for implantation in a body, and which is particularly adapted for use in a vessel such as the coronary sinus or cardiac great vein. The implantable medical device may take the form of a lead or catheter, and includes an extendable distal fixation member such as a helix. In one embodiment, the fixation member is a helix constructed of a shape memory metal or other super-elastic material. Upon deployment, the helix assumes a predetermined helix shape larger than the diameter of the lead body diameter. The helix functions to wedge or fix the lead within the vessel in a manner that does not impede the flow of blood through the vessel. The helix may be retracted for ease of repositioning and/or removal. In one embodiment of the invention, the fixation member may be advanced using a stiffening member such as a stylet. In another embodiment, the helix is coupled to a coiled conductor such that rotation of the conductor extends or retracts the helix. According to yet another aspect of the invention, a helix lumen including a flexible fluid-tight seal may be utilized to house the helix when it is in the retracted position.

33 Claims, 4 Drawing Sheets

U.S. PATENT DOCUMENTS

| | | | |
|---|---|---|---|
| 5,466,255 A | 11/1995 | Franchi | 607/128 |
| 5,522,874 A | 6/1996 | Gates | 607/127 |
| 5,522,875 A * | 6/1996 | Gates et al. | 607/127 |
| 5,522,876 A * | 6/1996 | Rusink | 607/127 |
| 5,549,642 A | 8/1996 | Min et al. | 607/5 |
| 5,716,390 A * | 2/1998 | Li | 607/127 |
| 5,716,391 A | 2/1998 | Grandjean | 607/127 |
| 5,837,006 A | 11/1998 | Ocel et al. | 607/127 |
| 5,871,531 A * | 2/1999 | Struble | 607/122 |
| 5,938,694 A * | 8/1999 | Jaraczewski et al. | 607/122 |
| 6,006,122 A | 12/1999 | Smits | 600/373 |
| 6,070,104 A | 5/2000 | Hine et al. | 607/123 |
| 6,119,042 A * | 9/2000 | Verness et al. | 607/122 |
| 6,161,029 A | 12/2000 | Spreigl et al. | 600/381 |

\* cited by examiner

SYSTEM AND METHOD FOR POSITIONING AN IMPLANTABLE MEDICAL DEVICE WITHIN A BODY

FIELD OF THE INVENTION

This invention relates to the field of body implantable medical device systems; and in particular, to a body implantable medical device system that includes an expandable helix and that is particularly designed for implantation into a vessel of the body.

BACKGROUND OF THE INVENTION

Modern electrical therapeutic and diagnostic devices for the heart, such as pacemakers, cardiovertors, and defibrillators, require a reliable electrical connection between the device and a region of the heart. Typically, a medical electrical lead is used for the desired electrical connection.

One type of commonly-used implantable lead is a transvenous lead generally taking the form of an elongated, substantially straight, flexible, insulated conductor. This type of lead is positioned through the venous system to attach to, and/or form an electrical connection with, the heart at the lead distal end. At the proximal end, the lead is typically connected to an implantable pulse generator. Because this type of lead may be placed through the venous system, electrical contact with the heart can be accomplished without requiring major thoracic surgery.

The specific design of a transvenous lead is generally dictated by the region of the heart in which it will be used. For example, U.S. Pat. No. 4,402,330 to Lindemans discloses a body implantable lead in which the lead body has a J-curve including a distal electrode with a permanent bend. This curve allows the lead to be readily positioned within, and connected to, the right atrium.

While the lead described in the '330 patent has been found acceptable for pacing the right atrium, a need exists for a similar transvenous medical electrical lead adapted for use in the left atrium. Such leads have been difficult to develop for a number of reasons. For example, minor blood clots are often caused by implanted objects placed within the vascular system. Should lead implantation cause blood clots to develop within the left side of the heart or associated vasculature, the direction of blood flow could cause these clots to be carried to the brain, causing stroke and other tissue damage. Thus, at present, chronic transvenous leads may not be safely implanted within the left side of the heart.

Despite the difficulties with lead placement, there remains a great need to be able to electrically stimulate and/or sense the left side of the heart since it accounts for the majority of the heart's hemodynamic output. For this reason, various pathologies may be better treated through stimulation on the left side of the heart. For example, in patients with dilated cardiomyopathy, electrical stimulation of both the right and left sides of the heart has been shown to be of major importance to improve the patient's well-being and to manage heart failure. See, for example, Cazeau et al., "Four Chamber Pacing in Dilated Cardiomyopathy," PACE, November 1994, pgs. 1974–79. See also Brecker and Fontainem, St. et al., "Effects Of Dual Chamber Pacing With Short Atrioventricular Delay In Dilated Cardiomyopathy," Lancet November 1992 Vol. 340 p1308–1312; Xiao H B et al., "Effect Of Left Bundle Branch Block On Diastolic Function In Dilated Cardiomyopathy," Br. Heart J 1991, 66(6) p 443–447; and Fontaine G et al, "Electrophysiology Of Pseudofunction," C. I. Meere (ed.) Cardiac pacing, state of the art 1979, Pacesymp, 1979 Montreal.

At present, there are several techniques for implanting a lead to the left side of the heart. For example, a median sternotomy, an intercostals approach, or, in a more limited procedure, a sub-xiphod approach may be used to place a lead on the external surface of the heart. These procedures, however, involve major surgery, which may be painful and dangerous for the patient, as well as extremely costly. The sub-xiphod approach, moreover, only permits limited access to the anterolateral surface of the left ventricle as well as to the left atrium.

An alternative approach involves electrically accessing the left atrium through the coronary sinus. Many catheter designs are available to facilitate lead placement in the coronary sinus. For example, U.S. Pat. No. 5,423,772 to Lurie, et. al. discloses a coronary sinus catheter having three sections. Each section has varying degrees of flexibility, with the proximal reinforced section being stiffer than an intermediate section, and the intermediate section being stiffer than a softened tip section. The catheter includes a curve extending from the intermediate section and continuing into the softened tip section, where the radius of curvature decreases. One drawback to such a design, however, is that the particular shape of the curve is not ideally suited for electrically accessing the left atrium. In addition, such a catheter is relatively complicated to manufacture because of the braid or other means that is required to reinforce the proximal section. Finally, such a catheter does not permit introduction of a stylet to assist in the placement of the catheter into the coronary sinus.

Another design is disclosed in U.S. Pat. No. 6,161,029 to Spreigl, et al. This design utilizes a balloon-expandable or self-expanding stent-like electrode that is deployed within the coronary sinus to distribute the electrode surface area over a wide area and to maintain the distal lead end in place. However, this type of lead is difficult to re-position or remove, as may be necessary to improve thresholds, to increase intrinsic signal amplitudes, or to replace the lead in the case of chronic problems such as lead failure or infection.

Yet another lead design is discussed in U.S. Pat. No. 6,006,122 to Smits. The disclosed lead utilizes a bent fixation ring positioned adjacent to a distal coronary sinus electrode. The ring, which is formed of a pliable material, is adapted to wedge or fix the lead within the coronary sinus in such a manner that the electrode is pushed against the vessel wall without impeding blood flow through the vessel. One of the drawbacks of this particular design is the inability to re-position and/or remove the electrode as may be required for any of the reasons discussed above.

U.S. Pat. No. 5,129,394 to Mehra describes a method and apparatus for sensing in vivo blood pressure proportional to the left ventricular pressure for detecting ventricular tachyarrhythmias or the cardiovascular status in congestive heart failure, and/or for adjusting the rate of a pacemaker. A lead with a pressure sensor near its distal end is placed transvenously through the coronary sinus and located in the coronary vein.

When in place, an inflatable balloon proximal to the pressure sensor may be used to acutely occlude the coronary vein until the sensor position is stabilized by the growth of fibrous tissue. According to this mechanism, the sensor may not be used for approximately six weeks until fibrous tissue has formed. After that, the lead may not be easily re-positioned or removed.

Other types of lead systems employ a shape memory-metal or other super elastic material designed to make the leads easier to deploy and affix. For example, U.S. Pat. No. 4,913,147 to Fahlstrom, et. al. describes a lead including one or more components formed of a shape-memory metal. These components are designed to have a first shape when at body temperature, and a second shape when at a different predetermined temperature. Such a component may be disposed at the distal lead end to assist in providing a reliable mechanical and electrical connection to the heart when the component changes shape. For example, this type of component may be disposed in proximity to the electrode to assume a first shape permitting easy introduction of the lead through a vein, and a second shape such as a curve that is adapted to maintain the electrode at a predetermined position within the heart or vascular system. In one disclosed embodiment of the device, the lead includes an extendable, non-expanding helix that remains smaller than the inner diameter of the lead lumen following deployment.

U.S. Pat. No. 5,522,876 to Rusink describes a lead for use with a pacemaker in a pacing system, the lead having at least one electrode and a helical fixation member at the lead distal tip. The helical member, which is adapted to be affixed to heart tissue, is composed of shape-memory metal. The helix is encapsulated within a mannitol or other dissolvable member in a shrunken state so that the helix diameter is less than the diameter of the lead casing. When the dissolvable member is dissolved by body fluids, the helix is released to assume an expanded diameter that is greater than the electrode diameter. When the helix is embedded into the heart wall, the helical coils are displaced radially away from the outer edge of the tip electrode so that the damage to the heart tissue immediately proximate to the tip electrode is minimized. One disadvantage of this system is that the helix is not retractable once it is deployed. Moreover, the design is adapted for use in the right ventricular or right atrial cardiac wall.

What is needed, therefore, is an improved lead adapted for use in the coronary sinus, middle and great cardiac veins, or another vessel that is both easy to deploy, and that may be readily removed and/or re-positioned.

It is thus an object of the present invention to provide a medical electrical lead that is suitably shaped to provide an electrical connection through the coronary sinus to one or both of the left chambers of the heart.

A still further object of the present invention is to provide a medical electrical lead having an electrode positioned so that when the lead is implanted into the coronary sinus, the electrode is positioned against the coronary sinus wall.

A still further object of the present invention is to provide a medical lead having a fixation method that may be extended and retracted to allow positioning and re-positioning of the lead.

A still further object of the present invention is to provide a medical lead having a fixation helix constructed of shape memory metal or other super elastic material that, upon extension, increases in diameter to the vessel wall, securing the lead in position.

A still further object of the present invention is to provide a medical electrical lead having an electrode that may be positioned along a selected portion of the coronary sinus wall in a manner that minimizes the restriction of blood flow through the coronary sinus.

SUMMARY OF THE INVENTION

These and other objects are accomplished through the present invention. In one embodiment, the present invention comprises an implantable medical device (IMD) such as a transvenous lead or catheter specifically designed for implantation within the body. While the inventive IMD and associated method of positioning the IMD may be used within a chamber of the heart such as the right ventricle, the invention is particularly suited for use in any body vessel, including the coronary sinus and cardiac great vein. The lead of the present invention includes an expandable fixation member such as a helix that may function as a pacing/sensing or a defibrillation electrode. The fixation member may be constructed of a shape memory metal or other super elastic material, and functions to wedge or fix the device within the coronary sinus or other vessel so that the fixation member is pushed against the vessel wall. The fixation member includes a central lumen so that the flow of blood through the vessel is not impeded. In alternative embodiments, the fixation member may be used for positioning only, as with defibrillation electrodes and/or sensors that are carried on a lead body. Alternatively, the current expandable fixation member may be usefully employed with any elongated implantable medical device, including catheters.

In one embodiment, the fixation member may be advanced using a stiffening member such as a stylet. The stiffening member is rotated to impart rotation to a helix in a manner that advances or retracts the helix. In another embodiment, the helix is coupled at a proximal end to a coiled conductor. Rotation of a proximal end of the conductor serves to extend or retract the helix. According to yet another aspect of the invention, a helix lumen including a flexible fluid-tight seal may be utilized to house the helix when it is in the retracted position. Additional aspects of the current invention will become apparent from the detailed description of the invention and the drawings.

DETAILED DESCRIPTION OF THE INVENTION

Figure 1:
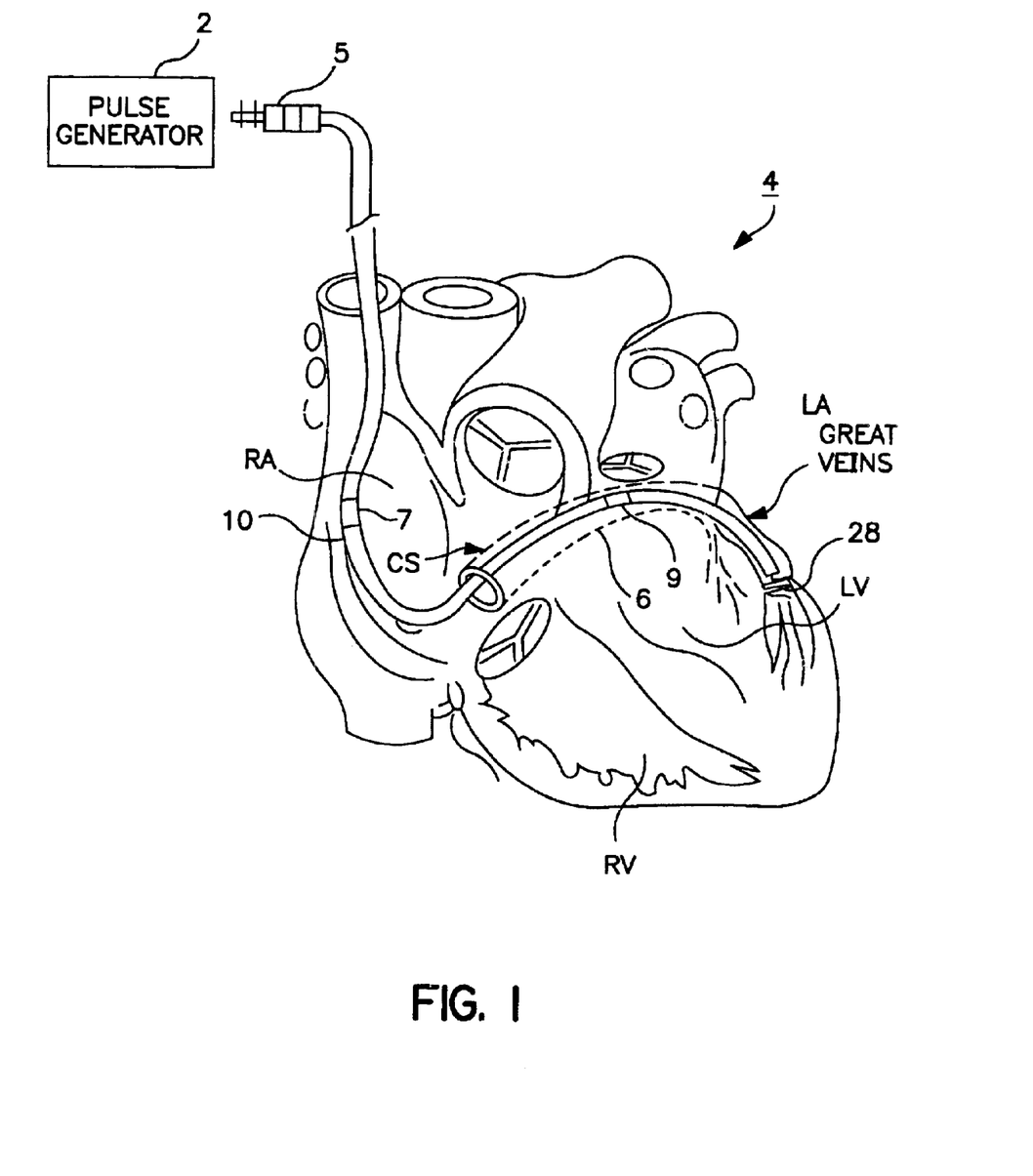
FIG. 1 is a perspective view of a lead according to the present invention implanted in a heart.

FIG. 1 is a perspective view of lead 10 according to the present invention, which is shown implanted in a heart 4. As seen in this embodiment, an implantable pulse generator 2 is coupled to a lead 10 by connector 5 as is well known in the art. Pulse generator 2 may be any model capable of sensing and stimulating two or more chambers of the heart 4 with at least one situated on the left side of heart 4. As further seen, in this embodiment, lead 10 may feature include one or more ring electrodes disposed along the lead body. In the illustrated embodiment, two ring electrodes 7 (right atrium) and 9 (left atrium) are shown. This embodiment further includes a helix 28 which extends beyond the distal end of the lead 10. Upon deployment, the helix expands and wedges within the coronary sinus, cardiac veins, or another vessel. This ensures excellent contact is maintained between the electrode 28 and the heart while also maintaining the lead 10 at the predetermined site of implant. The present invention permits the lead 10 to reliably pace and/or sense the right atrium, the left atrium, the left ventricle or any combination thereof by the electrodes 7, 9, and 28 respectively.

Figure 2:
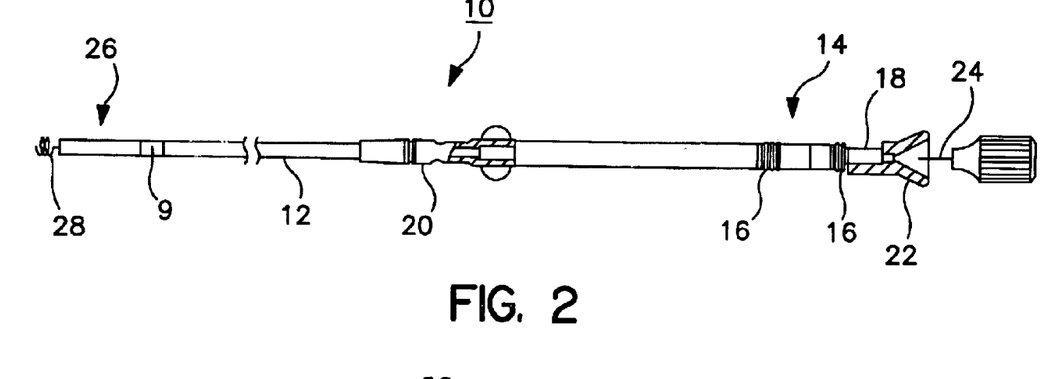
FIG. 2 is a plan view of the lead of FIG. 1, and further illustrates an implanting stylet assembly.

FIG. 2 is a plan view of one embodiment of the inventive lead. The bipolar lead 10 of this embodiment is stylet-activated, and includes an active fixation mechanism. Lead 10 further includes a flexible, elongate lead body 12 covered by an insulative sleeve, such as polyurethane or silicone rubber. Terminal assembly 14 is provided at the proximal end for coupling lead 10 to an implantable pulse generator 2 (FIG. 1). Terminal assembly 14 has sealing rings 16 and terminal pin 18, all of a type known in the art. An anchoring sleeve 20 (shown partially in cross-section) may also be provided for suturing lead body 12 to body tissue. Anchoring sleeve 20 and terminal assembly 14 are preferably fabricated from silicone rubber, although they may also be constructed of any other suitable biocompatible material known in the art.

The lead 10 of FIG. 2 is further shown to include stylet guide 22 and stylet assembly 24 coupled to terminal pin 18. The stylet assembly 24 imparts stiffness to lead 10 during placement. The stylet further actuates fixation helix 28 in a manner described below. Stylet guide 22 and stylet assembly 24 are typically discarded after use and before connection of terminal pin 18 to pulse generator 2 (FIG. 1). Other types of stiffening members as known in the art may be used in the alternative for this purpose.

With continued reference to FIG. 2, an electrode and fixation assembly designated generally as 26 is disposed at the distal end of lead body 12. In the illustrated embodiment, lead 10 is of the multi-polar, single pass configuration as may be adapted for placement in the coronary sinus or another vessel. The assembly 26 includes a distal helix electrode 28, and a ring electrode 9 positioned proximal to the distal end. As will be appreciated by those of ordinary skill in the art, helix electrode 28 and ring electrode 9 are coupled to separate, insulated lead conductors (not shown in FIG. 2) that extend substantially the length of lead body 12. Lead conductors are preferably configured as concentric multi-filar coils of a platinum-iridium alloy or any other suitable alloy, such as MP35N. This configuration allows for a longitudinal lumen that extends along the length of lead body 12 and that is adapted to receive stylet assembly 24. The lead may include one or more additional electrodes such as right atrium electrode 7 (FIG. 1).

Figure 3:
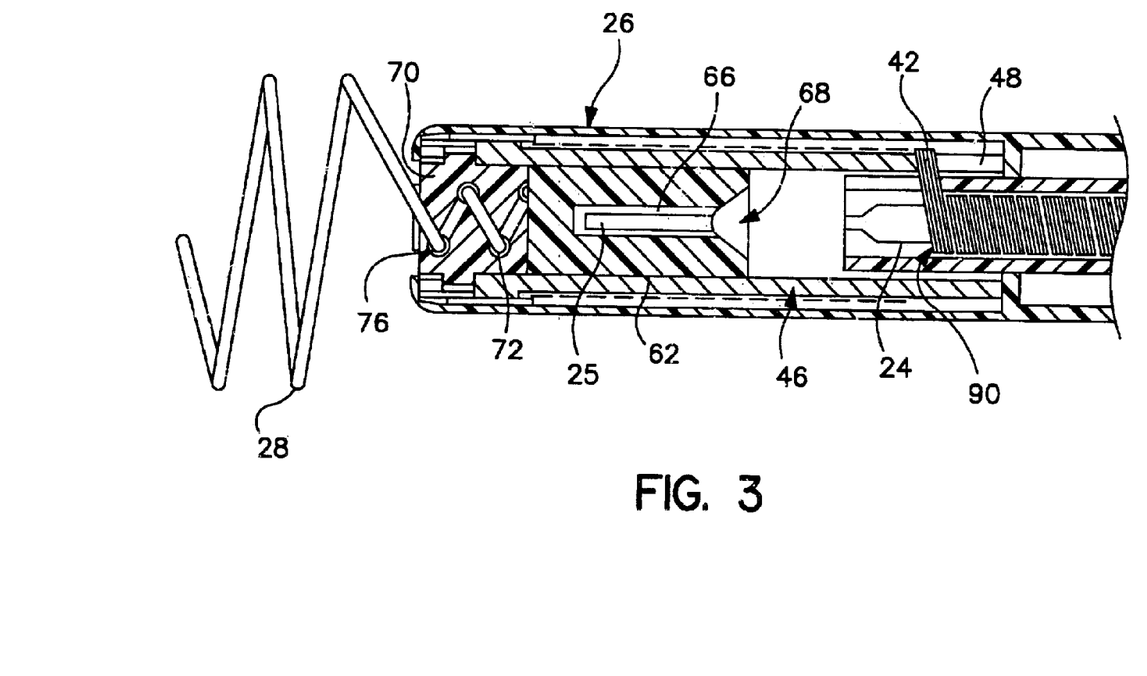
FIG. 3 is a cutaway side view of the inventive lead illustrating the helix in a deployed position.

FIG. 3 illustrates a cutaway side view of the fixation assembly 26 of lead 10 with helix 28 deployed. In this embodiment, fixation assembly 26 includes a stylet socket 62 that is slidably disposed in a piston-like fashion within the cylindrical interior of helix sleeve 46. Stylet socket is preferably made of hard plastic, which is molded to retain helix 28, which extends axially outward from stylet socket 62. Stylet socket 62 includes a coupling member such as axially-oriented slot 66 formed therein, which may include a flared opening 68 corresponding to screwdriver tip 25 of stylet 24.

The embodiment of FIG. 3 further includes a conductor coil 42 which defines a lumen for stylet 24. Conductor 42 terminates at helix sleeve 46. In one embodiment, helix sleeve 46 is made of machined polysulfone, and is provided with a rectangular slot 48 which allows the diameter of the coil defined by inner conductor 42 to increase at a "dog-leg" point designated generally as 90. Distally from "dog-leg" point 90, inner conductor 42 coils around the outer surface of helix sleeve 46 toward the distal end of helix sleeve 46, and is electrically coupled, e.g., by spot or laser welding, to helix 28.

Fixation assembly 26 may be retained within helix sleeve 46 by means of a substantially cylindrical helix seal 70 which may be formed of molded silicone rubber. Helix seal 70 is provided with a helical lumen or channel 72 extending from front to back, through which helix 28 is able to pass. Helical lumen 72 in helix seal 70 may be initially sealed at the distal end 76. When helix 28 advanced into helix seal 70 from the back, helix seal 70 guides helix 28 forward, such that the pointed tip of helix 28 pierces point 76 of lumen 72. When helix 28 is screwed back out, the resiliency of silicone rubber seal 70 is such that lumen 72 effectively seals itself. This self-sealing arrangement is believed to be advantageous in that it prevents body fluids from entering electrode and fixation assembly 26.

Helix 28 may be advanced and retracted using an embodiment of stylet 24 having a flattened tip 25. Rotation of the stylet imparts rotation to the helix assembly, causing the straightened helix to advance or retract. Upon exiting the distal end of the lead, the helix expands into a helical shape that makes solid contact with the vessel wall. The embodiment of fixation assembly and stylet illustrated in FIG. 3 are substantially described in U.S. Pat. Nos. 5,522,874 and 5,522,875 respectively to Gates, and which are hereby incorporated by reference in their entireties.

Transvenous implantation of lead 10 may be accomplished using conventional lead introduction techniques. During the implantation procedure, stylet 24 is used to provide stiffness to lead body 12, facilitating manipulation of lead 10 through the patient's venous system. Helix 28 is maintained in its most retracted position until the distal end of lead 10 including fixation assembly 26 is brought into contact with the desired coronary sinus, great vein, or other stimulation site. Since helix 28 is contained completely within the electrode and fixation assembly 26, it is prevented from damaging tissue as lead 10 is advanced through the venous system.

Once the desired electrode positioning is achieved, stylet 24 is rotated in the appropriate direction to cause helix 28 to advance through helical channel 72 within helix seal 70, eventually piercing a sealed portion at the distal end of helical channel 72 in the manner discussed above. Continued rotation of helix 28 will cause further advancement, so that helix 28 extends to its full diameter, engaging the endocardial vessel wall. In this way, electrode and fixation assembly 26, and in particular, helix electrode 28, is secured in contact with the desired stimulation site. To later remove or re-locate the lead, helix 28 can be released without significantly damaging the cardiac tissue by rotating stylet 24 in the opposite direction. Helix 28 re-assumes a compressed configuration when retracted within the lead inner lumen.

Figure 4:
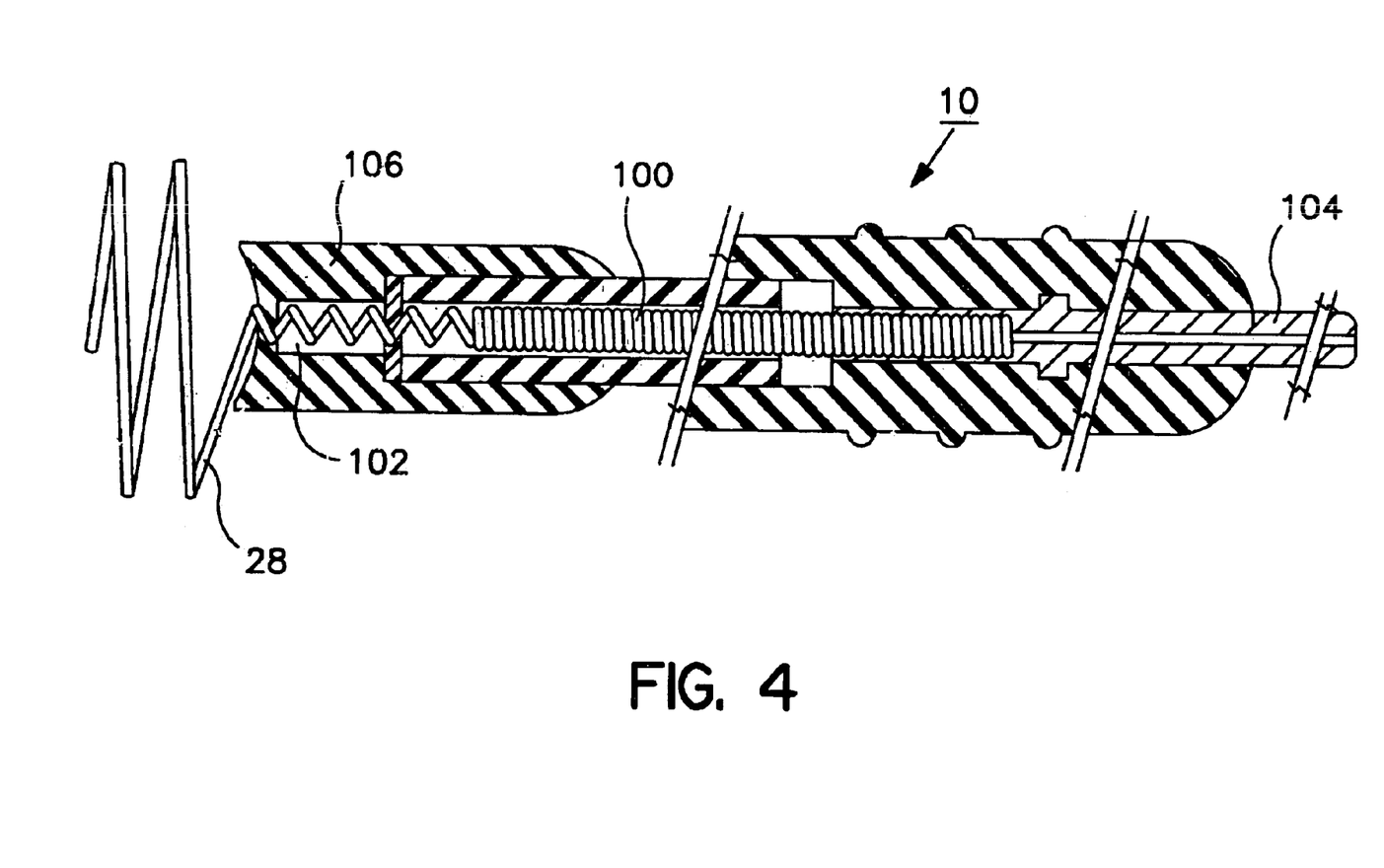
FIG. 4 is a cross-sectional view of the lead of FIG. 1 illustrating an alternative embodiment of a helix deployment assembly.

FIG. 4 is a cross-sectional view illustrating an alternative embodiment of the inventive lead. In this embodiment, fixation helix 28 is coupled to coiled conductor 100. The helix 28 is advanced or retracted out of a chamber or inner recess 102 in the distal end of the lead body 106 by rotation of the coiled conductor 100. This type of coil mechanism is disclosed in commonly assigned U.S. Pat. No. 4,106,512 to Bisping with improvements thereto disclosed in commonly assigned U.S. Pat. No. 4,311,153 to Smits, in U.S. Pat. No.

4,886,074 to Bisping, and in U.S. Pat. No. 5,837,006 to Ocel, all hereby incorporated by reference in their entireties. In these "Bisping" leads and the commercial embodiments thereof, rotation of the proximal end of a fixed pin 104 or other helix guide structure is utilized to impart rotational motion to the proximal end of coiled conductor 100. This rotation is, in turn, translated into axial advancement and retraction of the helix out of, and into, distal chamber 102. Upon exiting distal chamber 102 of lead 10, helix 28 expands into a helical shape wherein the helix is forced against a vessel wall such as the wall of the coronary sinus.

Yet another embodiment of a helix as may be employed with the current invention is shown in commonly-assigned U.S. Pat. No. 4,570,642 to Kane et al. hereby incorporated by reference in its entirety. According to this embodiment, the helix is fixed on a member slidably located within a chamber of the distal end of the pacing lead. A cylindrical stylet is employed to distally advance the slidable member within the chamber. This, in turn, exposes the fixation helix so that it may be screwed into the myocardium by rotation of the entire lead body.

Figure 5:
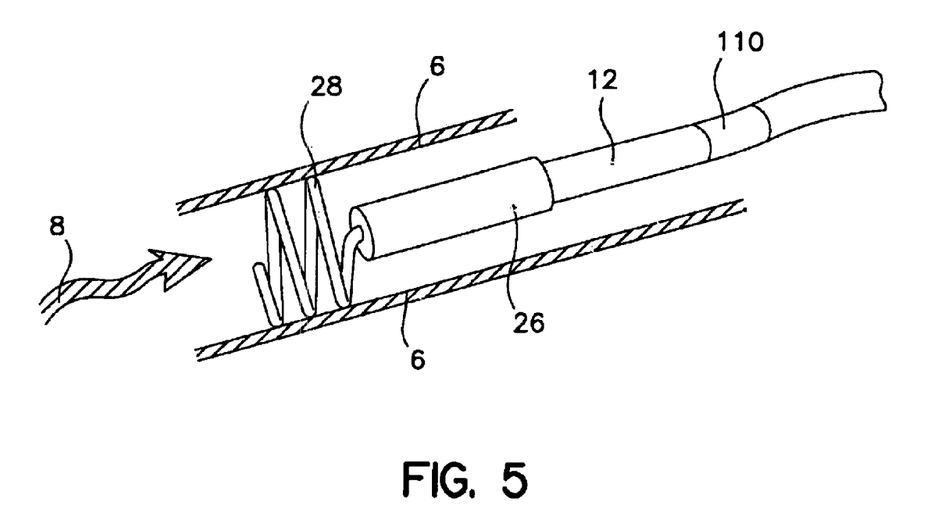
FIG. 5 is a plan view illustrating the lead of FIG. 1 located within a vessel when the helix is extended and expanded.

FIG. 5 is a plan view of fixation assembly 26 at distal end 12 of lead 10 implanted in a vessel such as the coronary sinus. As shown, helix 28 is sized to wedge against the coronary sinus walls 6 when deployed. The helix defines a lumen that permits the unimpeded flow of blood, as depicted by arrow 8. This uninterrupted blood flow prevents the formation of thrombosis and possible necrosis of the tissue, which may, in turn, cause stagnation in the vessel such that the health of the surrounding tissue is negatively impacted.

Figure 6:
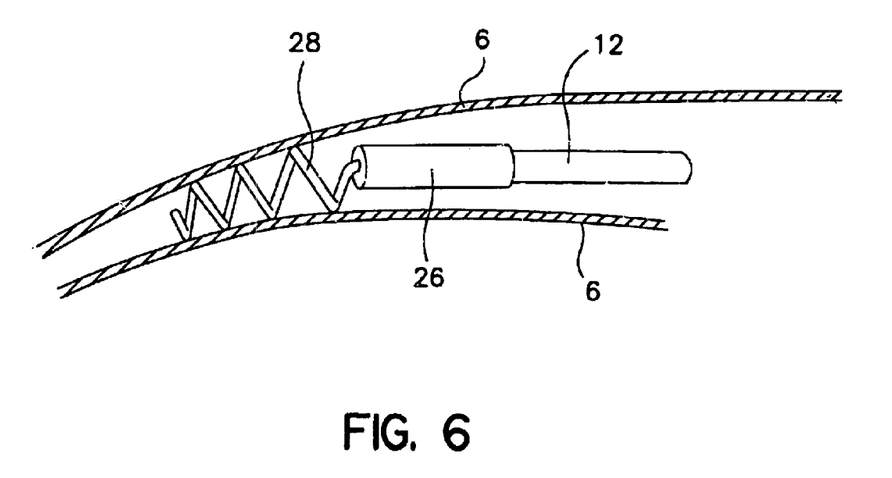
FIG. 6 is a plan view of a lead deployed within a vessel, wherein the helix electrode tapers from a larger diameter to a smaller diameter moving distally away from the lead.

FIG. 6 is a plan view of yet another embodiment of helix 28 wherein the helix has a decreasing diameter. This embodiment may be adapted for use in a portion of a vessel wherein the vessel is decreasing in size, for example. In the alternative, a helix having an increasing diameter towards the helix distal end may be utilized. Any other type of size variations along the length of the helix may likewise be utilized, such that only a portion of the helix diameter exceeds the diameter of the lead body.

Although the lead of FIG. 1 is shown as a pacing lead, one skilled in the art will appreciate that the current invention may be employed with many other embodiments of implantable leads, catheters, or other elongated implantable medical devices (IMDs) that are to be maintained chronically at a desired implant site. For example, a defibrillation lead connected to a defibrillator 2, as substantially described in U.S. Pat. No. 5,549,642 to Min, et al. and incorporated herein by reference in its entirety, may usefully employ the current invention. Alternatively, a helix formed of a nonconductive or conductive material may be employed to affix the distal end of a drug-delivery lead within the coronary sinus or another vessel. In yet another invention, the distal end of the fixation helix may be utilized to attach the associated IMD to tissue within a cardiac chamber such as the right ventricle. Many other alternative embodiments are also contemplated within the scope of the current invention.

In yet another embodiment of the current lead system, the lead body carries a sensing device such as sensor 110 (FIG. 5) to be placed in the coronary sinus or great vein. This is as substantially described in U.S. Pat. No. 5,129,394 to Mehra and incorporated herein by reference in its entirety. According to the described embodiment, a method and apparatus is provided for sensing in vivo blood pressure proportional to the left ventricular pressure. The measured pressure can be used to detect ventricular tachyarrhythmias or the cardio vascular status associated with congestive heart failure. Pressure measurements can also be used to adjust the rate at which pacing pulses are delivered. A lead with a pressure sensor near its distal end is placed transvenously through the coronary sinus and located in the coronary vein or great vein. The pressure that is sensed in that location is proportional to the left ventricular pressure. Values representing the left ventricular pulse, systolic and diastolic pressures, as well as the differentiated rate of change, dP/dt, gross rate of change, $\Delta P/\Delta t$, and mean or average pressure values are all, or selectively, developed by software algorithms and implemented in microprocessor-based control circuitry. In one preferred embodiment, one or more of the values are utilized in software-implemented algorithms to cause a pacemaker to pace the heart at a required rate to achieve a desired cardiac output. Alternatively, these left ventricular pressure-related values may be employed to confirm the absence of mechanical pumping action of the heart, which, in conjunction with other cardiac signals, confirm the existence of a tachyarrhythmia requiring anti-tachy pacing, cardioversion or defibrillation.

Many other types of sensors may be carried on a lead configured according to the current invention. Such sensors may measure $O_2$ saturation, temperature, flow, impedance, stroke volume, pH, and/or any of the other types of physiologic measurements known in the art. These sensors may be deployed, positioned and firmly anchored in the coronary sinus, middle and/or great cardiac vein, or another vessel using the current invention.

Although a specific embodiment of the invention has been disclosed, this is done for purposes of illustration only, and is not intended to be limiting with regards to the scope of the invention. It is contemplated various substitutions, alterations and/or modifications may be made to the disclosed embodiment without departing from the spirit and scope of the invention. Such modifications may include substituting elements or components that perform substantially the same function in substantially the same way to achieve substantially the same result as those described herein.

What is claimed is:

1. An implantable medical device (IMD) adapted for implantation within a body, comprising:
   an elongated body having a proximal end and a distal end, the distal end including an inner lumen;
   a helix residing within the inner lumen and adapted to be extended beyond the distal end of the elongated body, at least a portion of the helix having a diameter that is larger than the diameter of the elongated body when the helix is extended to aid in affixing the helix in an implantation; and
   a fixation assembly coupled to a proximal end of the helix and including a coupling member having a stylet interface slot wherein selective engagement with and rotation of the coupling member via the stylet interface slot, in a respective predetermined direction causes the helix to be extended and retracted, the fixation assembly being adapted to allow for retraction of the helix such that the helix re-assumes a compressed configuration within the inner lumen.

2. The IMD of claim 1, further comprising a stylet selectively engageable with the stylet interface slot, wherein the rotation of the coupling member is actuated by rotation of the stylet when the stylet is engaged with the stylet interface slot.

3. The IMD of claim 1, wherein the diameter of the helix when the helix is extended is substantially constant.

4. The IMD of claim 1, wherein the diameter of the helix when the helix is extended decreases towards a distal end of the helix.

5. The IMD of claim 1, and further including a conductor coupled to the helix whereby the helix may be used to deliver electrical stimulation.

6. The IMD of claim 5, wherein the conductor is a coiled conductor configured such that the helix may be extended and retracted by rotation imparted to a proximal end of the coiled conductor in a predetermined respective direction.

7. The IMD of claim 1, wherein the helix is formed of a super elastic material.

8. The IMD of claim 7, wherein the super elastic material is a shape memory alloy.

9. The IMD of claim 1, wherein the elongated body is further coupled to a sensor to sense a physiological signal.

10. The IMD of claim 9, wherein the sensor is selected from a group consisting of a pressure sensor, an $O_2$ saturation sensor, a temperature sensor, a flow sensor, an impedance sensor, a stroke volume sensor, and a pH sensor.

11. The IMD of claim 1, wherein the helix includes a lumen configured to allow blood flow to continue in an unimpeded manner at an implant site within the body.

12. The IMD of claim 1, and further including at least one ring electrode carried on the elongated body and coupled to a respective conductor to allow for multi-polar pacing.

13. The IMD of claim 12, wherein the at least one ring electrode includes a first ring electrode adapted to be located within the right atrium, and a second ring electrode adapted to provide electrical stimulation to the left atrium.

14. The IMD of claim 1, and further including at least one defibrillation electrode carried on the elongated body.

15. The IMD of claim 1, wherein the fixation assembly includes a helical lumen to guide the helix during extension and retraction.

16. The IMD of claim 15, wherein the helical lumen includes a seal adapted to prevent the ingress of fluids.

17. The IMD of claim 1, wherein the elongated body is a body of an implantable medical lead.

18. A method of retaining an implantable medical device (IMD) at a desired implant site within a body, wherein the IMD includes an elongated body having a distal end including a lumen, and an expandable helix residing within the lumen and having a coupling member coupled with a proximal portion of the helix, the method comprising:

guiding the distal end of the IMD to the desired implant site;

inserting a removable stylet through the elongated body to engage the coupling member;

advancing the helix beyond the distal end by actuating the stylet so that the helix expands, and wherein at least a portion of the helix has a diameter larger than the diameter of the elongated body to aid in affixing the helix.

19. The method of claim 18, wherein the coupling member includes a coiled conductor.

20. The method of claim 18, wherein actuating the stylet includes rotating the stylet.

21. The method of claim 18, and further including:

retracting the helix into the lumen; and moving the distal end of the elongated body.

22. The method of claim 21, wherein retracting includes compressing the helix.

23. The method of claim 18, wherein the helix is coupled to a conductor, and further including utilizing the advanced helix to deliver electrical stimulation to the body.

24. The method of claim 23, wherein the elongated body further carries a ring electrode, and wherein delivering electrical stimulation to the body includes delivering the electrical stimulation between the helix and the ring electrode.

25. The method of claim 24, wherein the elongated body carries multiple ring electrodes, and further including the method of utilizing one or more predetermined ones of the multiple ring electrodes to deliver electrical stimulation to one or more locations within the body other than the desired implant site.

26. The method of claim 18, wherein the elongated body carries a defibrillation electrode, and further including utilizing the defibrillation electrode to deliver electrical stimulation to the body.

27. The method of claim 18, wherein the elongated body includes a physiologic sensor, and further including utilizing the physiologic sensor to sense a physiological signal within the body.

28. The method of claim 18, wherein the implant site is located within a vessel of a body, and wherein step b.) includes expanding the helix to contact at least one wall of the vessel.

29. A medical lead adapted for implantation within the coronary sinus, comprising:

a lead body having a distal end that defines an inner recess;

an expandable helix residing within the inner recess that is adapted to be advanced outside the inner recess, at least a portion of the helix being capable of expanding to have a diameter that is larger than the diameter of the lead body to aid in affixing the helix; and a coupling member affixed to a proximal portion of the helix and including a stylet receiving slot, wherein selective engagement with and rotation of the coupling member via the stylet receiving slot allows the helix to be advanced.

30. The medical lead of claim 29, wherein the coupling member is adapted to allow for retraction of the helix such that the helix assumes a compressed configuration within the inner recess.

31. The medical lead of claim 29, and further including a conductor coupled to the helix, and wherein the helix is adapted to expand to contact at least one inner wall of the coronary sinus to deliver electrical stimulation thereto.

32. The medical lead of claim 31, and further including at least one ring electrode carried on the lead body.

33. The medical lead of claim 29, further including a physiological sensor carried on the lead body.

* * * * *